US00PP30014P3

(12) United States Plant Patent
Conner

(10) Patent No.: US PP30,014 P3
(45) Date of Patent: Dec. 25, 2018

(54) MUSCADINE GRAPE PLANT NAMED 'GA. 6-2-26'

(50) Latin Name: ***Vitus rotundifolia* Michx.**
Varietal Denomination: Ga. 6-2-26

(71) Applicant: University of Georgia Research Foundation, Inc., Athens, GA (US)

(72) Inventor: Patrick J. Conner, Tifton, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 15/731,308

(22) Filed: May 22, 2017

(65) Prior Publication Data

US 2018/0338399 P1 Nov. 22, 2018

(51) Int. Cl.
*A01H 5/08* (2018.01)
*A01H 6/88* (2018.01)

(52) U.S. Cl.
USPC ..... Plt./206
CPC ..... *A01H 6/88* (2018.05)

(58) Field of Classification Search
USPC ..... Plt./206
CPC ..... A01H 5/08; A01H 5/00; A01H 5/0812; A01H 6/88
See application file for complete search history.

*Primary Examiner* — June Hwu
(74) *Attorney, Agent, or Firm* — Klarquist Sparkman, LLP

(57) ABSTRACT

A new and distinct muscadine grape plant characterized by purple berries; self-fertile flowers; berries that separate with a high percentage of dry stem scars; berries that are very large in size; and very productive vines with high total and usable yields.

2 Drawing Sheets

Latin name: *Vitus rotundifolia* Michx.

BRIEF SUMMARY

The present invention comprises a new and distinct plant cultivar of *Vitis rotundifolia* Michx., which has been given the name 'Ga. 6-2-26'. My new variety has been asexually propagated in Tifton, Ga. by rooting cuttings under mist in the summer. The following unique combination of traits have been observed in the original plant of my variety and in asexually propagated progeny, when grown in Georgia, are firmly fixed, and which in combination distinguish it from existing cultivars:

1) Self-fertile flowers in combination with very large (approx. 15 grams) berry weight.
2) Purple colored berries.
3) Berries with a dry stem scar that separates cleanly from the pedicel.
4) Very productive vines with high total and usable yields.

Both Figures show the colors of the new variety as close to true color as is reasonably possible to obtain in colored reproductions of this type. Actual leaf and fruit colors may differ from leaf and fruit colors in the photograph due to light and environmental factors.

Figure 1:
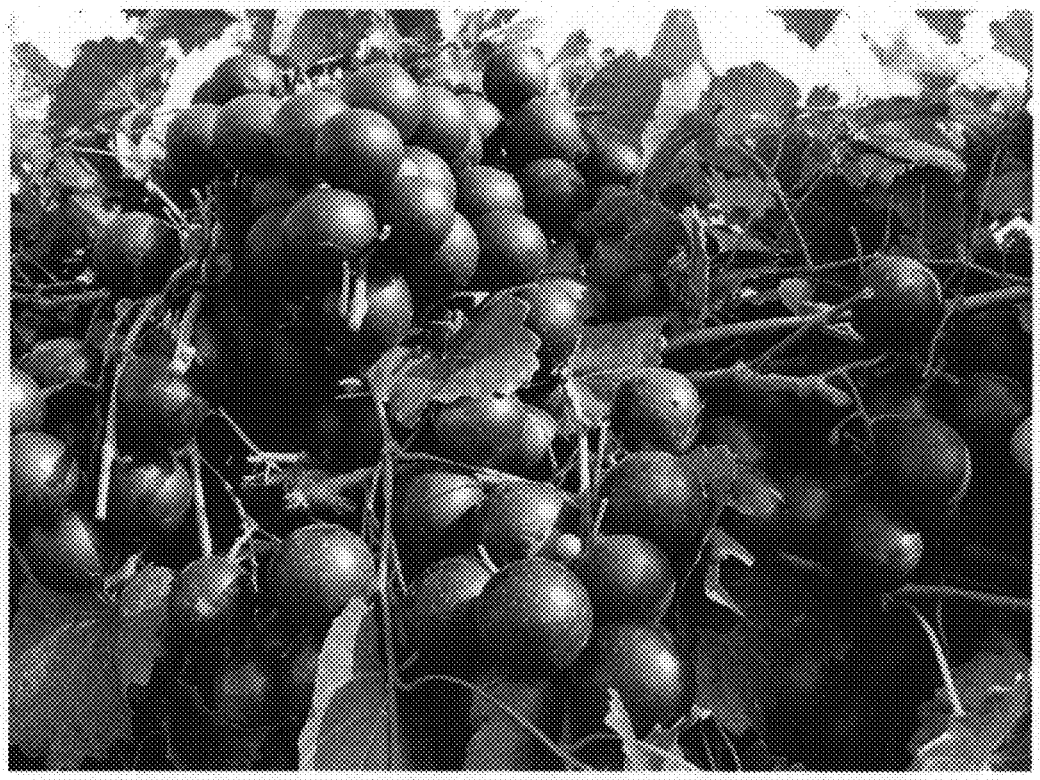
FIG. 1 is a detailed view of several clusters of ripe berries, obtained by clipping away some foliage.
Figure 2:
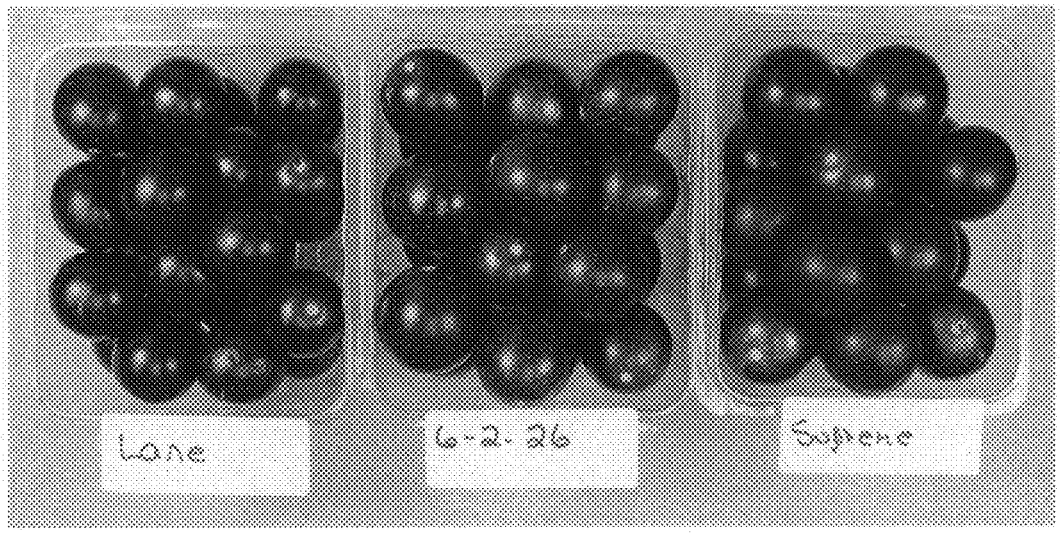
FIG. 2 is a view of ripe 'Ga. 6-2-26' berries (center) in a pint clamshell package in comparison to 'Ga. 5-1-45' (U.S. Plant Pat. No. 24,142) and 'Supreme' (U.S. Plant Pat. No. 7,267).

The illustrated vines of FIGS. 1 and 2 are six year old vines and the description is of six year old vines.

DETAILED DESCRIPTION

In the following description, color references are made to The Royal Horticultural Society Colour Chart, copyright 1966, except where general terms of ordinary dictionary significance are used.

BACKGROUND

The muscadine grape, *Vitis rotundifolia* Michx., is a popular fresh fruit grown in the Southeastern United States. In the Georgia climate, many cultivars ripen in early autumn when few other fruits are in season. The berries are large, as compared to other grape species, and are typically borne in clusters of 5-7 berries. Like many fruit crops, muscadine grapes are a heterozygous species and superior genotypes are clonally propagated. Nurseries typically propagate this species either by rooting softwood cuttings under mist, or by layering vines in the field.

The muscadine season in South Georgia begins in the last week of July and first week of August. At this time, growers begin picking the earliest ripening berries on the earliest cultivars. Unlike *vinifera* grapes, fresh-market muscadines are typically harvested as single berries by hand. Muscadines can vary in color from greenish-yellow (bronze) to pink, red, and purple, but stores often segregate them out as either bronze or purple/black. As consumers are often partial to one or the other color, a grower typically would like to have both colors available.

Numerous muscadine cultivars are of commercial importance. One muscadine production guide for Georgia lists 34 fresh market cultivars (nine are categorized as most recommended) and six processed grape cultivars. Even with this large number of cultivars, many are lacking desirable characteristics and growers are very interested in new cultivars with a higher combination of desirable traits. Currently, many commercial vineyards contain primarily female muscadine grape plants with a lesser number of self-fertile cultivars as the pollinator. Female cultivars have a yield that is often only about one-half that of self-fertile cultivars due to lack of pollination (flowers of female cultivars often don't open completely, blocking pollination). Despite the reduced productivity of most female cultivars, growers have continued to grow them because berry size and quality has typically been much larger in female cultivars than in self-fertile cultivars. Generally, growers want a berry size of at least 1 inch (2.5 cm) in diameter in a fresh-market cultivar. Provided minimum size and quality standards are met, more consistently productive self-fertile cultivars would be highly desirable.

DETAILED DESCRIPTION

An initial cross ('Supreme' x 'Tara') was made by the inventor at the University of Georgia, Tifton Campus as a part of a grape breeding program. 'Supreme' is the subject of U.S. Plant Pat. No. 7,267 and 'Tara' is unpatented. Approximately 200 seedlings from this cross were germinated in the greenhouse and planted at the Tifton campus in the spring of 2007. The original seedling vine of 'Ga. 6-2-26' was selected in 2009 for hermaphroditic flowers, large berry size, good productivity, dry stem scars, and long pedicels. In 2010, stem cuttings were rooted from the original seedling of this new variety in Tifton, Ga. Asexually propagated plants of the new variety were planted in trial plantings at two locations in Tifton, Ga. and at one location in Wray, Ga. in 2010. A trial planting of asexually propagated plants of the new variety was also made in 2011, in Athens, Ga.

'Ga. 6-2-26' is mid to late season muscadine with purple colored berries (FIGS. 1, 2) and hermaphroditic flowers. Yields of 'Ga. 6-2-26' are very good and are similar to other hermaphroditic cultivars and the high yielding female 'Supreme' (see Tables 1, 2 below). 'Ga. 6-2-26' produces a high percentage of usable yield (see Tables 1, 2 below) with low incidences of berry rot, and stem scar tears and splits (see Tables 3A, 3B, 4 below). Berry weight (15.3-15.5 g) and diameter (30.2-30.5 mm) is excellent and larger than other hermaphroditic cultivars (see Tables 3A, 3B, 4 below). Soluble solids of the berry juice was similar to the other cultivars tested (see Tables 3A, 3B, 4 below). Vine growth as measured by caliper is similar to 'Supreme' (see Tables 5, 6 below) but lower than some of the more vigorous cultivars such as 'Ga. 1-1-48' and 'Fry'.

Plant characteristics:

*Vines*.—The vines of 'Ga. 6-2-26' grow vigorously and mature canes in Tifton, Ga. are 1.4 to 1.8 m in length per growing season. Bark color is medium brown (RHS 199A) and rough in texture. Internode lengths are 5-6 cm in length. Tendrils are 8-10 cm long and unbranched, and discontinuous along the nodes. Tendril color is light green (RHS 141B). The young shoot has both downy hairs covering the leaf surface and erect hairs along the veins at the leaf base. Stem tissue of the shoot lacks hair. Shoot tip coloration is yellow-green (RHS 145A) with a pink purple blush (RHS 70B) due to the presence of anthocyanins.

*Foliage*.—Leaves average 60-62 mm in length and 85-90 mm in width. The leaves are circular with broadly toothed margins and glabrous on both upper and lower surfaces. Mature upper leaf surface is dark green (RHS 137A) and somewhat dull, while lower surfaces are light green (RHS 137C) and shiny. Petiole length is 4.9-6 cm and the petiole sinus is narrow or enclosed. The petiole color is yellow-green (RHS 152A).

*Flowers*.—The flowers are hermaphroditic. The petals are yellow green (RHS 145B) and small (with the inflorescence less than about 1 cm in diameter), which is typical for the species. The functional cream-colored anthers (RHS 158A) are supported on long (4 mm) filaments at the base of the ovary. The flowers are short lived, lasting approximately 2 to 3 days. 'Ga. 6-2-26' typically blooms from May 14th to June 1st at Tifton, Ga.

*Fruit*.—The vines produce very large (approx. 15 g) berries with purple color (RHS 187A-RHS 186A) at the base graduating towards purple-red at the stem end (RHS 58A). Average size of the fruit cluster is 5 to 12 cm in width and 7 to 13 cm in length. Average number of berries per cluster is eight and bunch density is very loose. Berries have moderately conspicuous lenticels over the entire berry surface. The berries ripen over a three week period beginning the third week of August in Tifton, Ga. The berries are round and average 30 mm in diameter, containing an average of 3 seeds per berry. Berry flesh is soft and juicy and yellow green (RHS 145C) in color and lacks anthocyanin coloration. Berries are easy to detach from the stem and have a sweet flavor and prominent fruity aroma. The seeds are yellow-green in color (RHS 152D). The berries separate from the pedicel with a dry stem scar. Fruit peduncles average 11.5 mm in length and are yellow brown in color (RHS N167A). Fruit pedicle is short (5-7 cm) and yellow brown (RHS N167A) in color. Fruit is primarily for fresh market use with short term cold storage up to 2 to 4 weeks.

*Disease resistence/hardiness*.—Symptoms of Pierce's disease (*Xylella fastidiosa*) have not been observed. Under a typical fungicide schedule, low levels of infection with bitter rot (*Greeneria uvicola*) Punithalingam, syn. *Melanconium fuligineum* and ripe rot (*Glomerella cingulata* were observed at Tifton, Ga. Only observed growing in USDA hardiness zone 8b. The plant is hardy in this zone. Hardiness has not been evaluated in other zones.

COMPARISONS WITH OTHER MUSCADINE GRAPE CULTIVARS

The Tables 1-6 below compare 'Ga. 6-2-26' with some other known muscadine grape cultivars. 'Fry' and 'Tara' are unpatented. 'Ga. 5-1-45' is the subject of U.S. Plant Pat. No. 24,142. 'Ga. 1-1-48' is the subject of U.S. Plant Pat. No. 27,033. 'Supreme' is the subject of U.S. Plant Pat. No. 7,267.

TABLE 1

Yield (kg/3-m vine) of 'Ga. 6-2-26' and standard muscadine cultivars at Tifton, GA in the third through seventh years of growth (2012-2016).

| Cultivar | No. vines | Total Yield (kg)[z] | Usable yield (kg)[yz] | Percent usable yield[z] |
|---|---|---|---|---|
| Year 3 | | | | |
| 'Ga. 6-2-26' | 8 | 17.3 | 15.3 a | 88.7 a |
| 'Fry' | 4 | 11.7 | 7.0 c | 55.9 d |
| 'Ga. 1-1-48' | 4 | 14.6 | 10.3 bc | 74.0 bc |
| 'Ga. 5-1-45' | 4 | 12.9 | 8.4 c | 67.2 cd |
| 'Supreme' | 4 | 12.8 | 10.3 bc | 81.0 ab |
| 'Tara' | 3 | 19.1 | 14.7 ab | 76.7 abc |
| Significance | | NS | 0.001 | 0.001 |
| Year 4 | | | | |
| 'Ga. 6-2-26' | 8 | 20.6 ab | 19.2 ab | 93.6 |
| 'Fry' | 4 | 8.7 d | 6.7 d | 77.7 |
| 'Ga. 1-1-48' | 4 | 21.2 ab | 19.5 ab | 92.1 |
| 'Ga. 5-1-45' | 4 | 13.5 cd | 9.6 cd | 71.3 |
| 'Supreme' | 4 | 25.1 a | 23.0 a | 91.4 |
| 'Tara' | 3 | 16.5 bc | 14.7 bc | 88.5 |
| Significance | | 0.001 | 0.001 | NS |
| Year 5 | | | | |
| 'Ga. 6-2-26' | 8 | 31.0 a | 28.4 a | 91.7 a |
| 'Fry' | 4 | 13.8 cd | 11.6 bc | 82.8 bc |
| 'Ga. 1-1-48' | 4 | 22.9 b | 17.7 c | 76.7 c |
| 'Ga. 5-1-45' | 4 | 20.2 bc | 17.0 bc | 83.6 bc |
| 'Supreme' | 4 | 24.2 b | 21.4 ab | 88.7 ab |
| 'Tara' | 3 | 24.5 b | 21.8 ab | 88.9 ab |
| Significance | | 0.001 | 0.001 | 0.001 |
| Year 6 | | | | |
| 'Ga. 6-2-26' | 8 | 34.1 | 28.1 | 84.0 a |
| 'Fry' | 4 | 33.5 | 22.1 | 67.5 b |
| 'Ga. 1-1-48' | 4 | 29.7 | 24.9 | 68.1 b |
| 'Ga. 5-1-45' | 4 | 23.0 | 17.9 | 75.3 ab |
| 'Supreme' | 4 | 28.7 | 21.9 | 83.2 a |
| 'Tara' | 3 | 33.1 | 27.9 | 79.4 ab |
| Significance | | NS | NS | 0.01 |
| Year 7 | | | | |
| 'Ga. 6-2-26' | 8 | 30.7 | 25.6 | 83.3 ab |
| 'Fry' | 4 | 25.9 | 15.5 | 60.0c |
| 'Ga. 1-1-48' | 4 | 24.0 | 20.7 | 85.8 ab |
| 'Ga. 5-1-45' | 4 | 19.2 | 15.5 | 80.6 b |
| 'Supreme' | 4 | 25.3 | 21.0 | 84.5 ab |
| 'Tara' | 3 | 31.1 | 27.4 | 87.9 a |
| Significance | | NS | NS | 0.001 |
| All Years | | | | |
| 'Ga. 6-2-26' | 8 | 26.4 a | 25.3 a | 87.5 a |
| 'Fry' | 4 | 18.6 b | 14.3 c | 69.6 c |
| 'Ga. 1-1-48' | 4 | 22.5 ab | 20.8 b | 83.6 ab |
| 'Ga. 5-1-45' | 4 | 18.0 b | 15.1 c | 78.3 b |
| 'Supreme' | 4 | 22.7 ab | 21.7 ab | 86.5 a |
| 'Tara' | 3 | 25.3 a | 23.8 ab | 86.5 a |
| Significance | | 0.003 | 0.001 | 0.001 |

[z]Mean separation within columns by Duncan's multiple range test, $P < 0.05$.

[y]Usable yield is total yield minus weight of rotted berries and berries with pedicel scar splitting.

TABLE 2

Yield (kg/6.1-m vine), at Wray, GA in the third through seventh years of growth (2012-2016).

| Cultivar | No. vines | Total Yield (kg)[z] | Usable yield (kg)[yz] | Percent usable yield[z] |
|---|---|---|---|---|
| Year 3 | | | | |
| 'Ga. 6-2-26' | 2 | 36.8 | 33.8 | 92.2 a |
| 'Ga. 1-1-48' | 4 | 26.9 | 22.3 | 83.6 a |
| 'Supreme'[x] | 4 | 17.7 | 14.9 | 84.9 a |
| 'Tara' | 4 | 16.3 | 11.4 | 70.1 b |
| Significance | | NS | NS | 0.034 |
| Year 4 | | | | |
| 'Ga. 6-2-26' | 2 | 11.8 | 10.3 | 90.5 |
| 'Ga. 1-1-48' | 4 | 20.6 | 14.3 | 69.9 |
| 'Supreme'[x] | 4 | 22.1 | 19.9 | 89.5 |
| 'Tara' | 4 | 15.4 | 11.3 | 71.6 |
| Significance | | NS | NS | NS |
| Year 5 | | | | |
| 'Ga. 6-2-26' | 2 | 40.9 | 37.8 | 92.3 |
| 'Ga. 1-1-48' | 4 | 27.5 | 23 | 83.8 |
| 'Supreme'[x] | 4 | 30.2 | 22.5 | 75.1 |
| 'Tara' | 4 | 40.4 | 21.3 | 61.9 |
| Significance | | NS | NS | NS |
| Year 6 | | | | |
| 'Ga. 6-2-26' | 2 | 60.3 a | 51.0 a | 83.8 |
| 'Ga. 1-1-48' | 4 | 67.3 a | 54.0 a | 80.6 |
| 'Supreme'[x] | 4 | 0[w] b | 0 b | ND[v] |
| 'Tara' | 4 | 61.1 a | 32.0 a | 53.1 |
| Significance | | 0.002 | 0.002 | NS |
| Year 7 | | | | |
| 'Ga. 6-2-26' | 2 | 93.9 a | 82.3 a | 87.7 |
| 'Ga. 1-1-48' | 4 | 39.8 b | 39.8 b | 72.9 |
| 'Supreme'[x] | 4 | ND[v] | ND[v] | ND[v] |
| 'Tara' | 4 | 8.7 b | 8.7 b | 68.3 |
| Significance | | 0.001 | 0.001 | NS |
| All Years | | | | |
| Ga .6-2-26' | 2 | 48.7 | 43.1 a | 89.3 a |
| 'Ga. 1-1-48' | 4 | 39.3 | 30.7 ab | 78.2 a |
| 'Supreme' | 4 | ND[v] | ND[v] | ND[v] |
| 'Tara' | 4 | 35.0 | 21.0 b | 65.0 b |
| Significance | | NS | 0.01 | 0.001 |

[z]Mean separation within columns by Duncan's multiple range test.

[y]Usable yield is total yield minus weight of rotted berries and berries with pedicel scar splitting.

[x]'Supreme' was planted in 2011 and is a year behind the other cultivars.

[w]'Supreme' overcropped in year 5 and in 2016 vines were weak or dead with no crop.

[v]No Data

Tables 3A and 3B describe flower and fruit attributes of 'Ga. 6-2-26' and standard muscadine cultivars at Tifton, Ga. in the third through seventh years of growth (2012-2016).

TABLE 3A

| Cultivar | Flower type[z] | Berry color | Avg. day of first harvest | Berry rot (%)[y] | Berry stem scar split (%)[y] |
|---|---|---|---|---|---|
| 'Ga. 6-2-26' | H | Black | Aug. 20 a | 8 b | 4 c |
| 'Fry' | F | Bronze | Aug. 16 b | 16 a | 18 a |
| 'Ga. 1-1-48' | H | Bronze | Aug. 2 c | 17 a | 3 c |
| 'Ga. 5-1-45' | H | Black | Aug. 3 c | 4 c | 22 a |
| 'Supreme' | F | Black | Aug. 18 ab | 4 c | 13 b |
| 'Tara' | H | Bronze | Aug. 4 c | 10 b | 5 c |
| Significance | | | 0.001 | 0.001 | 0.001 |

[z](H) hermaphroditic, (F) female

TABLE 3B

| TABLE 3BCultivar | Berry stem scar tear (%)[y] | Dry scar (%)[y] | Berry wt. (g)[y] | Berry diam. (MM)[y] | Percent soluble solids of all harvests[y] |
|---|---|---|---|---|---|
| 'Ga. 6-2-26' | 11 d | 85 ab | 15.5 a | 30.2 a | 14.2 |
| 'Fry' | 34 a | 48 d | 11.7 b | 27.4 b | 14.0 |
| 'Ga. 1-1-48' | 8 d | 90 a | 10.2 cd | 26.0 cd | 14.5 |
| 'Ga. 5-1-45' | 23 c | 55 c | 9.6 d | 25.6 d | 15.3 |
| 'Supreme' | 29 b | 59 c | 15.1 a | 29.9 a | 14.3 |
| 'Tara' | 12 d | 83 b | 10.8 bc | 26.4 c | 13.9 |
| Significance | 0.001 | 0.001 | 0.001 | 0.001 | NS |

[y]Mean separation within columns by Duncan's multiple range test.

TABLE 4

Vine caliper (mm) of Ga. 1-1-48 and standard muscadine cultivars after the first three years of growth at Tifton, GA.

| Cultivar | 2011 caliper (mm)[z] | 2012 caliper (mm)[z] | 2013 caliper (mm)[z] |
|---|---|---|---|
| 'Ga. 1-1-48' | 7.2c | 23.9 | 33.4 |
| 'Fry' | 11.6 a | 26.5 | 35.1 |
| 'Ga. 5-1-45' | 8.4 bc | 22.8 | 30.5 |
| 'Tara' | 10.6 ab | 26.4 | 33.3 |
| 'Triumph' | 9.7 abc | 24.8 | 35.5 |
| Significance | 0.031 | NS | NS |

[z]Caliper measured on the trunk 75 cm above ground before budbreak. Mean separation within columns by Duncan's multiple range test, $P < 0.05$, with $n = 4$.
NS = Nonsignificant

TABLE 5

Vine caliper (mm) of 'Ga. 6-2-26' and standard muscadine cultivars after the first six years of growth at Tifton, GA, in years 2011-2016.

| Cultivar | 2011 | 2012 | 2013 | 2014 | 2015 | 2016 |
|---|---|---|---|---|---|---|
| 'Ga. 6-2-26' | 7.9c[z] | 19.5 b | 29.3 | 32.9 b | 37.3 | 40.0 b |
| 'Fry' | 11.6a | 26.5 a | 35.1 | 28.1 a | 39.1 | 41.5 ab |
| 'Ga. 1-1-48' | 7.2 c | 23.9 ab | 33.4 | 36.5 ab | 37.8 | 44.4 a |
| 'Ga. 5-1-45' | 8.4 bc | 22.8 ab | 30.5 | 33.1 b | 36.8 | 38.2 b |
| 'Supreme' | 8.5 bc | 23.9 ab | 29.8 | 37.0 ab | 38.2 | 41.5 ab |
| 'Tara | 10.6 ab | 26.4 a | 33.3 | 40.7 a | 41.5 | 41.1 ab |
| Significance | 0.006 | 0.038 | NS | 0.008 | NS | 0.04 |

[z]Caliper measured on the trunk 75 cm above ground before budbreak. Mean separation within columns by Duncan's multiple range test.
NS = Nonsignificant

TABLE 6

Vine caliper (mm) of 'Ga. 6-2-26' and standard muscadine cultivars after the first six years of growth at Wray GA, in years 2011-2016.

| Cultivar | 2011 | 2012 | 2013 | 2014 | 2015 | 2016 |
|---|---|---|---|---|---|---|
| 'Ga. 6-2-26' | 6.1 | 16.0 | 26.2 | 28.6 ab[z] | 30.8 ab | 31.9 |
| 'Ga. 1-1-48' | 7.0 | 20.4 | 27.5 | 30.9 a | 33.7 ab | 34.9 |
| 'Supreme'[y] | 5.1 | 18.3 | 24.4 | 24.7 b | 26.6 b | |
| 'Tara' | 6.7 | 20.3 | 27.3 | 31.1 a | 32.9 ab | 41.2 |
| Significance | NS | NS | NS | 0.034 | 0.006 | NS |

[z]Caliper measured on the trunk 75 cm above ground before budbreak. Mean separation within columns by Duncan's multiple range test.
NS = Nonsignificant
[y]'Supreme' was planted in 2011 and is a year behind the other cultivars.

What is claimed is:

1. A new and distinct muscadine grape plant, as herein illustrated and described, characterized by purple berries; self-fertile flowers; berries that separate with a high percentage of dry stem scars; berries that are very large in size; and very productive vines with high total and usable yields.

* * * * *

'Ga. 5-1-45' 'Ga. 6-2-26' 'Supreme'